United States Patent [19]

Feldman et al.

[11] Patent Number: 5,516,953
[45] Date of Patent: May 14, 1996

[54] PROCESS FOR THE PREPARATION OF OPTICALLY ACTIVE CYCLOOLEFINS

[75] Inventors: Jerald Feldman, Hockessin; William A. Nugent, Jr., Wilmington, both of Del.

[73] Assignee: E. I. Du Pont de Nemours and Company, Wilmington, Del.

[21] Appl. No.: 207,535

[22] Filed: Mar. 8, 1994

[51] Int. Cl.$^6$ ..................................................... C07C 6/02
[52] U.S. Cl. ........................ 585/366; 585/365; 585/374; 585/375; 585/643; 585/646
[58] Field of Search ................................. 585/365, 366, 585/374, 375, 376, 637, 643, 645, 646

[56] References Cited

U.S. PATENT DOCUMENTS

| | | | |
|---|---|---|---|
| Re. 26,875 | 5/1970 | Calderon | 260/666 |
| 3,631,209 | 5/1972 | Frech et al. | 585/366 |
| 3,660,509 | 5/1972 | Anganbright | 585/366 |
| 3,974,231 | 8/1976 | Küepper et al. | 585/366 |
| 4,550,216 | 10/1985 | Basset et al. | 585/645 |
| 5,082,909 | 1/1992 | Bell | 526/169 |

FOREIGN PATENT DOCUMENTS

| | | |
|---|---|---|
| 0084437 | 1/1983 | European Pat. Off. |
| 2499083 | 2/1986 | France |
| 3229419 | 8/1982 | Germany |
| 6313418 | 8/1982 | Japan |
| 63-44735 | 9/1988 | Japan |

OTHER PUBLICATIONS

Nugent, W. A., et al, *Science*, 259, 479–483, 1993.
Noyori, R., *Chemtech*, 22, 360–367, 1992.
Corey, E. J. et al, *The Logic of Chemical Synthesis*, John Wiley and Sons, New York, 1989.
Schurig V., *Isreal Journal of Chemistry*, 15, 96–98, 1976/77.
Waters et al., *Tetrahedron Lett.*, 1968, pp. 5233–5236.
Consiglio et al, *Helv. chim. Acta.*, 63, Fasc. 4, No. 5, 987–989, 1980.
Ivin, K. J., *Olefin Metathesis*, Academic Press, London, 1983, Chapter 7.6, pp. 144–148.
Finkel'shtein et al, *Izv. Akad. Nauk SSR, Ser, Khim.*, No. 3, pp. 641–645, Mar. 1981.
Kawai et al, *Journal of Catalysis*, 89, 452–461, 1984.
Fu, G. C., et al, *J. Am. Chem. Soc.*, 114, 7324–7325, 1992.
Fu, G. C., et al, *J. Am. Chem. Soc.*, 114, 5426–5427, 1992.
Fu, G. C., et al, *J. Am. Chem. Soc.*, 115, 3800–3801, 1993.
Couturier et al, *Angew, Chem. Int. Ed. Engl.*, 32(1), 112–115, 1993.
Nguyen, S. T. et al, *J. Am. Chem. Soc.*, 115, 9858–9859, 1993.
Brown, H. C. et al, Richard B. Wetherill Labroatory, Purdue University, *Communications To The Editor*, vol. 84, 4341–4342, Nov. 20, 1962.
Oskam, J. H., et al, *J. Organometallic Chem.*, 459, 185–198, 1993.
Bell, A., *J. Mol. Catal.*, 76, 165–180, 1992.
Kress, J., et al, *J. Mol. Catal.*, 36(1), 1986.
Kress, J., et al, *J. Chem. Soc., Chem. Comm.*, 514–516, 1982.
Aguero, A., et al., *J. Chem. Soc., Chem. Comm.*, 793–794, 1985.
Verkuijlen, E., et al, *Recl. Trav. Chim. Pays–Bas*, 96(8), M86–M90, 1977.
Otton, J. et al, *J. Mol. Catal.*, 8(313), 1980.
Quignard, F., et al, *J. Chem. Soc., Chem. Commun.*, 1816–1817, 1985.
Quignard, F., et al, *Journal of Molecular Catalysis*, 36, 13–29, 1986.
Mol. J. C., *Chemtech*, 250–255, Apr. 1983.
Schrock, R. R., et al, *Macromolecules*, 20, 1169–1172, 1987.
Van Roosmalen, A. J., *Journal of Molecular Catalysis*, 8, 185–190, 1980.
Schrock, R. R., et al. *J. Am. Chem. Soc.*, 110, 1423–1435, 1988.

*Primary Examiner*—Ponnathapura Achutamurthy

[57] ABSTRACT

A process for the preparation of optically active cycloolefins based upon reaction of optically active dienes in the presence of catalyst compositions comprising molybdenum and tungsten complexes.

14 Claims, No Drawings

PROCESS FOR THE PREPARATION OF OPTICALLY ACTIVE CYCLOOLEFINS

FIELD OF INVENTION

This invention relates to the preparation of optically active cycloolefins from optically active dienes.

BACKGROUND OF INVENTION

Enantiopure chiral intermediates are of major importance in the pharmaceutical and agrichemical industries. Such intermediates can be further elaborated to provide exclusively the biologically active enantiomer of a drug or crop protection chemical. This both eliminates waste in the manufacturing process and circumvents potential deleterious side-effects arising from the undesired enantiomer. W. A. Nugent et al., *Science*, 259, 479 (1993), R. Noyori, *CHEMTECH*, 22, 360 (1992). One potentially valuable class of chiral intermediate which has heretofore been unavailable are the enantiopure methylcycloalkenes. For example, the Nobel laureate E. J. Corey has noted the potential utility of enantiopure 3-methylcyclopentene and the derived trans-epoxide in asymmetric synthesis. E. J. Corey and X. Cheng, *The Logic of Chemical Synthesis*, John Wiley and Sons, New York, 1989.

Prior to the present invention, 3-methyl-cyclopentene had not been prepared selectively and with high enantiopurity. Acetoxylation of (R)-3-methylcyclopentanol, followed by pyrolysis at 530° C. of the resulting acetate afforded a mixture of enantiopure (+)-(R)-3-methyl-cyclopentene and 4-methylcyclopentene in a 3:2 ratio; the mixture could not be separated by distillation (V. Schurig *Israel Journal of Chemistry* 1976/77, 15, 96). Kinetic resolution of racemic -methyl-cyclopentene by asymmetric hydroboration afforded material with low optical purity (Brown et al., 84, 4341; Waters et al., *Tetrahedron Lett.*, 1968, 5233). Asymmetric alkylation of an allylic ether gave 3-methylcyclopentene with very low optical purity (Congsiglio et al., *Helv. Chim. Acta.*, 1980, 63, 987).

The present invention makes possible the trivial synthesis of chiral cycloolefins selectively and in optical purities difficult or impossible to achieve by other routes. It is based on the ring-closing metathesis reaction of terpene derived, optically active dienes. Although intramolecular cyclization of dienes to give cycloolefins via metathesis is known, it has never been used to make optically active cycloolefins. The intramolecular cyclization of dienes containing two double bonds separated by five single bonds, to give cyclohexene, is well known. This literature is summarized in the book K. J. Ivin, *Olefin Metathesis*, Academic Press, London, 1983, Chapter 7.6. Ring-closing metathesis of dienes containing two double bonds separated by 4 single bonds, to give 5-membered rings, is not as well known (Finkel'shtein et al., *Izv. Akad. Nauk SSR, Ser, Khim.*, 1981, 641; Kawai et al., 1984, 89, 452; Fu et al., *J. Am. Chem. Soc.*, 1992, 114, 7324; Fu et al., *J. Am. Chem. Soc.*, 1992, 114, 5426; Fu et al., *J. Am. Chem. Soc.*, 1993, 115, 3800; Couturier et al., *Angew. Chem. Int. Ed. Engl.*, 1993, 32, 112).

The present invention differs from the prior art in several respects. First, the product formed is optically active. Second, the double bonds of the diene undergoing ring-closing metathesis are highly hindered: one double bond is tri-substituted and the other may be one bond removed from a tertiary carbon atom, as is the case in β-citronellene. Therefore, the reaction might have been anticipated to proceed in poor yield due to steric hindrance. In the prior art, the double bonds of dienes undergoing ring-closing metathesis are never more than disubstituted, and in fact are almost always monosubstituted. Thus, this invention differs from the prior art in that one of the olefins being formed in the reaction is isobutylene. Third, we disclose herein a highly active catalyst system [$WOCl_2$ ($O-2,6-C_6H_3-Br_2)_{2/MR\ 4}$] for the ring-closing reaction that is very easy to prepare, in contrast to several other catalysts for this general type of reaction which require multiple steps to be synthesized (Fu et. al. *J. Am. Chem. Soc.* 1992, 114, 7324; Fu et. al. *J. Am. Chem. Soc.* 1992, 114, 5426; Fu et. al. *J. Am. Chem. Soc.* 1993, 115, 3800; Couturier et. al. *Angew. Chem. Int. Ed. Engl.* 1993, 32, 112).

SUMMARY OF THE INVENTION

This invention provides a process for the preparation of an optically active cycloolefin, comprising contacting an optically active diene of formula I

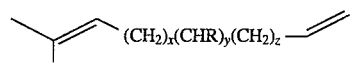

wherein
R is a $C_1$ to $C_{20}$ hydrocarbyl optionally substituted with nitrogen or oxygen atoms;
x and z are independently 0, 1, 2, 3, or 4;
y is 1, 2, 3, 4, or 5; and wherein the sum of x, y and z is less than or equal to 5;
with a catalyst composition comprising one of Mo(V) Mo(VI) or W(VI) bearing covalently bound ligands selected from O, $OR^1$, $NR^2$, Cl, Br, $CR^3R^4$ and $R^5$, wherein
$R^1$ and $R^2$ are independently a $C_1$ to $C_{20}$ hydrocarbyl optionally substituted with F, Cl, Br or I;
$R^3$ and $R^4$ are independently H or a $C_1$ to $C_{20}$ hydrocarbyl; and
$R^5$ is a $C_1$ to $C_{20}$ hydrocarbyl;
wherein said catalyst composition optionally comprises a cocatalyst selected from $SnR^6R^7R^8R^9$, $PbR^6R^7R^8R^9$, $AlR^6R^7R^8$, $MgR^6R^7$ and $ZnR^6R^7$;
wherein $R^6$–$R^9$ are independently H, a $C_1$ to $C_{20}$ hydrocarbyl, Cl, Br or I; to yield an optionally active cycloolefin of formula II

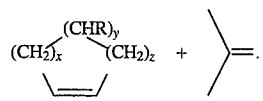

DETAILED DESCRIPTION OF THE INVENTION

In describing the process of the invention, Applicants intend to convey the following meanings to the terms employed throughout this application.

By metathesis Applicants mean "the interchange of carbon atoms between a pair of double bonds" (K. J. Ivin, Olefin Metathesis, Academic Press, 1983).

By the term "hydrocarbyl", Applicants include all alkyl, aryl, aralkyl or alkylaryl carbon substituents, either straight-chained, cyclic, or branched, and substituted accordingly with hydrogen atoms.

By the term "chiral" Applicants mean "existing as a pair of enantiomers." The enantiomers or stereoisomers, are designated the R and S isomers, and are nonsuperimposable mirror images of one another. A chiral material may either contain an equal amount of the R and S isomers in which case it is called "racemic" or it may contain inequivalent amounts of R and S isomer in which case it is called "optically active," or "nonracemic."

By the term "enantiomeric excess" ("ee"), Applicants mean the absolute difference between the percent of R enantiomer and the percent of S enantiomer of an optically active compound. For example, a compound which contains 75% S isomer and 25% R isomer will have an enantiomeric excess of 50%. Within the process of the present invention, the optical activity (or "ee" value) of the product cycloolefin will be a direct result of the optical activity of the diene used as the substrate. For example, in the present process an optically pure diene will yield an optically pure cycloolefin.

As used herein the term "optically pure" refers to an enantiomeric excess greater than 99%.

This invention provides a process for preparation of optically active cycloolefins. Examples are 3-methyl-cyclopentene and 4-methyl-cyclohexene from terpene derived, optically active dienes, as shown in the equations below:

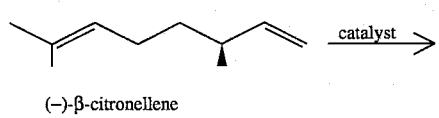

(−)-β-citronellene

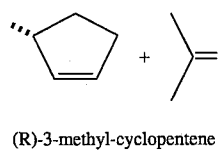

(R)-3-methyl-cyclopentene

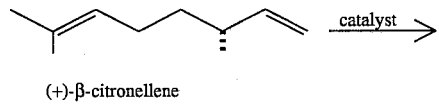

(+)-β-citronellene

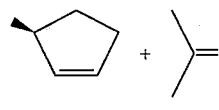

(S)-3-methyl-cyclopentene

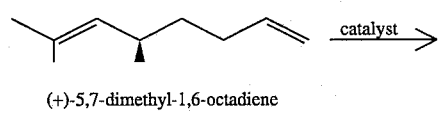

(+)-5,7-dimethyl-1,6-octadiene

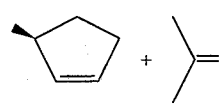

(S)-3-methyl-cyclopentene

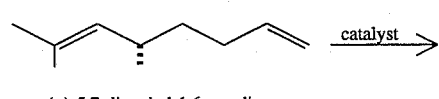

(−)-5,7-dimethyl-1,6-octadiene

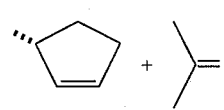

(R)-3-methyl-cyclopentene

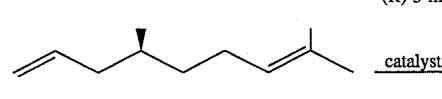

(S)-2,6-dimethyl-2,8-nonadiene

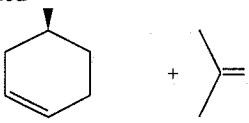

(S)-4-methyl-cyclohexene

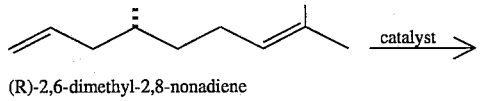

(R)-2,6-dimethyl-2,8-nonadiene

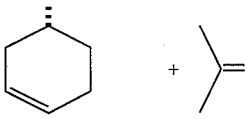

(R)-4-methyl-cyclohexene

The process for preparation of optically active cycloolefins from optically active dienes is shown in the equation below:

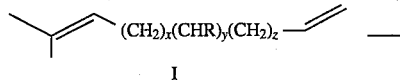

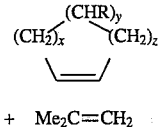

$+ Me_2C=CH_2$ wherein
R is a $C_1$ to $C_{20}$ hydrocarbyl optionally substituted with nitrogen or oxygen atoms;
x and z are independently 0, 1, 2, 3, or 4;
y is 1, 2, 3, 4, or 5; and the sum of x, y and z is less than or equal to 5.

The stereochemistry of the product hydrocarbyl-substituted cycloolefin formed in these reactions is determined by the stereochemistry of the diene substrate.

The optically active dienes of the process are available commercially (e.g., Fluka Chemical Co., Ronkonkoma, N.Y.) or may be prepared by methods known in this art, as further demonstrated in Examples 1, 3, and 6 herein.

The process of the invention can be carried out under reduced pressure or at pressures between 101 and 1000 kPa; pressures between 50 and 500 kPa are preferred. The process is preferably carried out in an organic solvent; examples of suitable organic solvents include benzene, toluene, xylene, chlorobenzene, ortho-dichlorobenzene, and 1,2-dichloroethane. The process is preferably carried out under an inert atmosphere, preferably nitrogen or argon. The reaction is carried out over a temperature range of 0° to 150° C., with a range of 25° to 130° C. preferred. In the reaction a ratio of starting diene to catalyst is in the range of 20 to 1000. When a cocatalyst is used, the ratio of cocatalyst to catalyst will be between 1 to 1 and 2 to 1.

The process uses a catalyst composition containing a Mo(V), Mo(VI), or W(VI) metal which bears covalently bound ligands selected from O, $OR^1$, $NR^2$, Cl, Br, $CR^3R^4$ and $R^5$ and optionally contains $SnR^6R^7R^8R^9$, $PbR^6R^7R^8R^9$, $AlR^6R^7R^8$, $MgR^6R^7$ or $ZnR^6R^7$ cocatalyst wherein
$R^1$ and $R^2$ are independently a $C_1$ to $C_{20}$ hydrocarbyl optionally substituted with F, Cl, Br, or I;
$R^3$–$R^4$ are independently H or a $C_1$ to $C_{20}$ hydrocarbyl;
$R^5$ is a $C_1$ to $C_{20}$ hydrocarbyl;

$R^6$–$R^9$ are independently H, $C_1$ to $C_{20}$ hydrocarbyl, Cl, Br, or I.

By "Mo(V)" Applicants mean a molybdenum complex in the formal +5 oxidation state, and with a d electron configuration of one. By "Mo(VI)" Applicants mean a molybdenum complex in the formal +6 oxidation state, and with a d electron configuration of zero. By "W(VI)" Applicants mean a tungsten complex in the formal +6 oxidation state, and with a d electron configuration of zero. By "formal oxidation state" Applicants mean the charge that would be left on the transition metal if all ligands were removed in their closed shell configurations. For purposes of electron counting Applicants regard $OR^1$, Cl, Br, and $R^5$ as bearing a minus one charge; and O, $NR^2$ and $CR^3R^4$ as bearing a minus two charge. A more detailed description of "formal oxidation state" and "d electron configuration" may be found in J. P. Collman, L. S. Hegedus, J. R. Norton, and R. G. Finke, Principles and Applications of Organo-transition Metal Chemistry, University Science Books, 1987, Chapter 2.1.

An example of a Mo(V) complex is $MoCl_5$. Examples of Mo(VI) complexes are $MoO_2Cl_2$, $MoOCl_4$, $MoO_3$, and Mo(CH-t-Bu) (N-2,6-$C_6H_3$-i-$Pr_2$) $[OCMe(CF_3)_2]_2$. Examples of W(VI) complexes are $WCl_6$, $WOCl_4$, W(N$C_6H_5$)$Cl_4$, $WCl_4$(O-2,6-$C_6H_3$-i-$Pr_2$)$_2$, and $WOCl_2$(O-2, 6-$C_6H_3$-$Br_2$)$_2$.

The catalyst composition may optionally comprise the cocatalysts $SnR^6R^7R^8R^9$, $PbR^6R^7R^8R^9$, $AlR^6R^7R^8$, $MgR^6R^7$, or $ZnR^6R^7$. These cocatalysts may be readily prepared from commercially known chemical methods. Cocatalysts may be necessary when the catalytically active species (a transition metal carbene complex) is to be generated in situ.

Optically active methylcycloalkenes which are accessible via the present invention can serve as valuable intermediates in the synthesis of enantiopure drugs and crop protection agents. Such biologically active compounds are frequently cyclic or polycyclic derivatives which often bear methyl groups as substituents. The optically active methylcycloalkenes offer the opportunity to prepare such compounds by selective functionalization of the carbon-carbon double bond.

The following non-limiting Examples demonstrate the process of the invention.

EXAMPLE 1

This example demonstrates the preparation of R-(−)-citronellene (also available commercially from the Fluka Chemical Company). The starting material, R-(−)-citronellyl bromide, is available commercially from the Aldrich Chemical Co., Milwaukee, Wis., USA. To a stirred solution of R-(−)-citronellyl bromide (25 g, 114 mmol) in 150 mL tetrahydrofuran was added potassium tert-butoxide (19.2 g, 171 mmol) over the course of several minutes. The reaction mixture was stirred for 2 days at room temperature. Water (500 mL) was added to the reaction mixture, which was then extracted two times with 100 mL of pentane. The pentane extract was dried over $MgSO_4$, and the pentane then removed by distillation under nitrogen. The resulting crude product was doubly distilled under an atmosphere of nitrogen at 165°–166° C. to afford R-(−)-citronellene (8.81 g, 56%). At a concentration of 8.40 g/100 mL $CHCl_3$, the product's optical rotation was measured to be −9.7°±0.1°, confirming that it was the R-(−) enantiomer.

EXAMPLE 2

This example demonstrates the ring-closing metathesis reaction of R-(−)-citronellene to give R-(+)-3-methylcyclopentene. Under nitrogen, a round bottom flask was charged with 60 mL chlorobenzene, R-(−)-citronellene prepared in Example 1 (8.56 g, 61.9 mmol), and $WOCl_2$ (O-2,6-$C_6H_3$-$Br_2$)$_2$ (0.96 g, 1.22 mmol); a solution of tetraethyllead (0.80 g, 2.45 mmol) in 5.0 mL chlorobenzene was added last. A water-cooled reflux condenser was attached to the round bottom flask, and the reaction mixture heated at 90° C. for 2 h. The reaction mixture was then cooled to room temperature and filtered through a ¼" column of silica gel. The volatile reaction products (boiling point <100° C.) were separated from chlorobenzene by distillation. The distillate was refluxed gently for 1 h under a water cooled condenser to remove any isobutylene, and redistilled at 60°–64° C. to remove any remaining chlorobenzene, affording 3.01 g of a colorless liquid (36.6 mmol, 59%). This material was determined to be 3-methylcyclopentene by $^1$H NMR comparison with an authentic sample. At a concentration of 5.23 g/100 mL $CHCl_3$, the product's optical rotation was measured to be 167.4°±0.2°, confirming that it was the R-(+) enantiomer.

A sample of R-(+)-3-methylcyclopentene, prepared in this manner, in methylene chloride was epoxidized using a stoichiometric amount of meta-chloroperbenzoic acid; the resulting mixture of diastereomeric epoxides was resolved on a chiral capillary GLC column (Chiraldex G-TA, 20 m), and from the peak areas it was determined that the R-(+)-3-methylcyclopentene prepared by this method was formed with enantiomeric excess (ee)=97%.

EXAMPLE 3

This example demonstrates the preparation of S-(+)-citronellene (also available commercially from the Fluka Chemical Company). The starting material, S-(+)-citronellyl bromide, is available commercially from the Aldrich Chemical Co., Milwaukee, Wis., USA. To a stirred solution of S-(+)-citronellyl bromide (25 g, 114 mmol) in 150 mL tetrahydrofuran was added potassium tert-butoxide (19.2 g, 171 mmol) over the course of several minutes. The reaction mixture was stirred for 3 days at room temperature. Water (500 mL) was added to the reaction mixture, which was then extracted two times with 100 mL of pentane. The pentane extract was dried over $MgSO_4$, and the pentane then removed by distillation under nitrogen. The resulting crude product was doubly distilled under an atmosphere of nitrogen to afford S-(+)-citronellene (9.63 g, 61%). At a concentration of 9.53 g/100 mL $CHCl_3$, the product's optical rotation was measured to be 10.7°±0.2°, confirming that it was the S-(+) enantiomer.

EXAMPLE 4

This example demonstrates the ring-closing metathesis reaction of S-(+)-citronellene to give S-(−)-3-methylcyclopentene. Under nitrogen, a round bottom flask was charged with 45 mL 1,2,4-trichlorobenzene, S-(+)-citronellene prepared in Example 3 (9.38 g, 67.8 mmol), and $WOCl_2$(O-2, 6-$C_6H_3$-$Br_2$)$_2$ (1.12 g, 1.42 mmol); a solution of tetraethyllead (0.94 g, 2.88 mmol) in 5.0 mL chlorobenzene was added last. A water-cooled reflux condenser was attached to the round bottom flask, and the reaction mixture heated at 90° C. for 2 h. The reaction mixture was then cooled to room temperature and filtered through a ½" column of silica gel. The volatile reaction products were separated by distillation. The distillate was refluxed gently for 1 h under a water cooled condenser to remove any isobutylene, affording 3.13 g of a colorless liquid (38.0 mmol, 61%). This material was determined to be 3-methylcyclopentene by $^1$H and $^{13}$C NMR comparison with an authentic sample. At a concentration of 5.14 g/100 mL CHCl$_3$, the product's optical rotation was measured to be $-166.6°\pm0.2°$, confirming that it was the S-(–) enantiomer.

EXAMPLE 5

This example demonstrates the ring-closing metathesis reaction of (+)-5,7-dimethyl-1,6-octadiene (Fluka) to give S-(–)-3-methylcyclopentene. Under nitrogen, a round bottom flask was charged with 50 mL ortho-dichlorobenzene, (+)-5,7-dimethyl-1,6-octadiene (6.57 g, 47.5 mmol), WOCl$_2$(O-2,6-C$_6$H$_3$-Br$_2$)$_2$ (0.73 g, 0.95 mmol), and tetraethyllead (0.62 g, 1.90 mmol). A water-cooled reflux condenser was attached to the round bottom flask, and the reaction mixture heated at 90° C. for 2 h. The reaction mixture was then cooled to room temperature and filtered through a ½" column of silica gel. Distillation of the filtrate afforded 1.45 g of a clear oil boiling at 50°–60° C.: by $^1$H NMR it was determined that this material was 3-methylcyclopentene, contaminated by 29 wt. % of isobutylene. The optical rotation of this material was $-75.9°\pm0.4°$ (4.66 g/100 mL CHCl$_3$), confirming that it was the S-(–) enantiomer.

EXAMPLE 6

This example demonstrates the synthesis of (S)-4,8-dimethyl-1,7-nonadiene from S-(–)-citronellal (Aldrich). A sidearm flask was charged with triphenylmethylphosphonium bromide (22.9 g, 64.1 mmol) and 400 mL tetrahydrofuran; this solution was put under a nitrogen atmosphere and cooled to $-20°$ C. To this was added 38 mL of a 1.6M solution of n-butyllithium in ether. The resulting reaction mixture was allowed to warm to room temperature, stirred for 30 min, and then cooled to $-78°$ C. S-(–)-Citronellenal (11.0 mL, 61 mmol) was then added by syringe. The reaction mixture was stirred for 1 h at $-78°$ C. and then allowed to warm slowly to room temperature. Acetone (10 mL) was then added, and the reaction mixture allowed to stir for an additional 30 min. Finally, 800 mL of hexane was added and the reaction mixture filtered. The filtrate was concentrated in vacuo to afford (S)-4,8-dimethyl-1,7-nonadiene (5.63 g, 60%) as a clear oil.

EXAMPLE 7

This example demonstrates the ring-closing metathesis reaction of (S)-4,8-dimethyl-1,7-nonadiene to give (S)-4-methylcyclohexene. A round bottom flask was charged under nitrogen with 40 mL ortho-dichlorobenzene, (S)-4,8-dimethyl-1,7-nonadiene (3.50 g, 23.0 mmol), WOCl$_2$(O-2,6-C$_6$H$_3$-Br$_2$)$_2$ (0.36 g, 0.46 mmol), and tetraethyllead (0.30 g, 0.92 mmol). A water-cooled reflux condenser was attached to the round bottom flask, and the reaction mixture heated at 90° C. for 2 h. The reaction mixture was then cooled to room temperature and filtered through a ½" column of silica gel. Distillation of the filtrate afforded a clear oil. This material was determined by $^1$H NMR to be 4-methylcyclohexene. A sample of this material in methylene chloride was epoxidized using a stoichiometric amount of metachloroperbenzoic acid; the resulting mixture of diastereomeric epoxides was resolved on a chiral HPLC column, and from the peak areas it was determined that the (R)-4-methylcyclohexene prepared in this example was formed with enantiomeric excess (ee) $\geq 99\%$.

EXAMPLE 8

This example demonstrates the ring-closing metathesis reaction of S-(+)-citronellene to give S-(–)-3-methylcyclopentene. S-(+)-Citronellene (36 mg, 0.26 mmol) and Mo(CHCMe$_2$Ph) (N-2,6-C$_6$H$_3$-i-Pr$_2$) [OCMe(CF$_3$)$_2$]$_2$ (10 mg, 0.013 mmol) were dissolved in 1 mL of toluene-d8. The resulting solution was heated under nitrogen for 1 h at 90° C. The solution was then cooled to room temperature and its $^1$H NMR spectrum recorded; this showed isobutylene and 3-methylcyclopentene to be the only reaction products, and no unreated S-(+)-citronellene. The Mo(CHCMe$_2$Ph) (N-2,6C$_6$H$_3$-i-Pr$_2$) [OCMe(CF$_3$)$_2$]$_2$ and related Mo catalysts can be prepared by methods commonly known in the art, e.g., J. H. Oskan et al., J. Organometallic Chem., 459, 195–198 (1993).

What is claimed is:

1. A process for the preparation of an optically active cycloolefin, comprising contacting an optically active diene of formula I

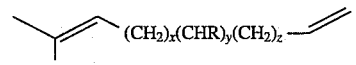

wherein the sum of x and z is 2 or greater and

R is a C$_1$ to C$_{20}$ hydrocarbyl group optionally substituted with nitrogen or oxygen containing functional groups;

x and z are independently 0, 1, 2, 3, or 4;

y is 1, 2, 3, 4, or 5; and wherein the sum of x, y and z is less than or equal to 5;

with a catalyst composition comprising one of Mo(V) Mo(VI) or W(VI) bearing covalently bound ligands selected from O, OR$^1$, NR$^2$, Cl, Br, CR$^3$R$^4$, and R$^5$, wherein at least two of the groups bound to Mo or W are OR$^1$, wherein R$^1$ and R$^2$ are independently a C$_1$ to C$_{20}$ hydrocarbyl group optionally substituted with F, Cl, Br or I;

R$^3$ and R$^4$ are independently H or a C$_1$ to C$_{20}$ hydrocarbyl group; and R$^5$ is a C$_1$ to C$_{20}$ hydrocarbyl group;

wherein said catalyst composition optionally comprises a cocatalyst selected from SnR$^6$R$^7$R$^8$R$^9$, PbR$^6$R$^7$R$^8$R$^9$, AlR$^6$R$^7$R$^8$, MgR$^6$R$^7$ and ZnR$^6$R$^7$;

wherein R$^6$–R$^9$ are independently H, a C$_1$ to C$_{20}$ hydrocarbyl group, Cl, Br or I;

to yield an optically active cycloolefin of formula

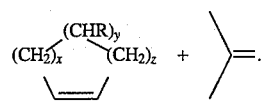

2. The process of claim 1 wherein the catalyst composition comprises W(VI), and a cocatalyst.

3. The process of claim 2 wherein the catalyst composition comprises W(VI) covalently bearing an O, two Cl or two Br, and two OR$^1$ groups wherein each R$^1$ is a halo substituted phenyl.

4. The process of claim 2 wherein the catalyst composition comprises WCl$_6$, WOCl$_4$, W(NC$_6$H$_5$)Cl$_4$, WCl$_4$(O-2,6-C$_6$H$_3$-i-Pr$_2$)$_2$, or WOCl$_2$(O-2,6-C$_6$H$_3$-Br$_2$)$_2$, and a cocatalyst.

5. The process of claim 4 wherein the catalyst composition comprises WOCl$_2$(O-2,6-C$_6$H$_3$-Br$_2$)$_2$ and Pb(CH$_2$CH$_3$)$_4$.

6. The process of claim 1 wherein the catalyst composition comprises Mo(V) or Mo(VI).

7. The process of claim 6 wherein the catalyst composition is Mo[CHC(CH$_3$)$_2$C$_6$H$_3$](N-2,6-C$_6$H$_3$-i-Pr$_2$) [OCH$_3$(CF$_3$)$_2$]$_2$, MoO$_2$Cl$_2$, MoOCl$_4$, MoO$_3$, or MoCl$_5$.

8. The process of claim 1 wherein the diene of formula I is (−)-β-citronellene and the optically active cycloolefin prepared by the process is (R)-3-methyl-cyclopentene.

9. The process of claim 1 wherein the diene of formula I is (+)-β-citronellene and the optically active cycloolefin prepared by the process is (S)-3-methyl-cyclopentene.

10. The process of claim 1 wherein the diene of formula I is (+)-5,7-dimethyl-1,6-octadiene and the optically active cycloolefin prepared by the process is (S)-3-methyl-cyclopentene.

11. The process of claim 1 wherein the diene of formula I is (−)-5,7-dimethyl-1,6-octadiene and the optically active cycloolefin prepared by the process is (R)-3-methyl-cyclopentene.

12. The process of claim 1 wherein the diene of formula I is (S)-2,6-dimethyl-2,8-nonadiene and the optically active cycloolefin prepared by the process is (S)-4-methyl-cyclohexene.

13. The process of claim 1 wherein the diene of formula I is (R)-2,6-dimethyl-2,8-nonadiene and the optically active cycloolefin prepared by the process is (R)-4-methyl-cyclohexene.

14. The process of claims 8, 9, 10, 11, 12 or 13, wherein the diene is optically pure and the cycloolefin prepared by the process is optically pure.

\* \* \* \* \*

UNITED STATES PATENT AND TRADEMARK OFFICE
CERTIFICATE OF CORRECTION

PATENT NO. : 5,516,953
DATED : May 14, 1996
INVENTOR(S) : Jerald Feldman and William A. Nugent, Jr.

It is certified that error appears in the above-identified patent and that said Letters Patent is hereby corrected as shown below:

<u>Claim 4, Column 8, lines 57-58</u>:
    Change "$WCl_6$, $WOCl_4$, $W(NC_6H_5)Cl_4$, $WCl_4(O\text{-}2,6\text{-}C_6H_3\text{-}i\text{-}Pr_2)_2$, or $WOCl_2(O\text{-}2,6\text{-}C_6H_3\text{-}Br_2)_2$"
    to --$WCl_4(O\text{-}2,6\text{-}C_6H_3\text{-}i\text{-}Pr_2)_2$ or $WOCl_2(O\text{-}2,6\text{-}C_6H_3\text{-}Br_2)_2$--.

<u>Claim 7, Column 8, lines 66-67</u>:
    Change "$Mo[CHC(CH_3)_2C_6H_3](N\text{-}2,6\text{-}C_6H_3\text{-}i\text{-}Pr_2)[OCH_3(CF_3)_2]_2$, $MoO_2Cl_2$, $MoOCl_4$, $MoO_3$, or $MoCl_5$"
    to --$Mo[CHC(CH_3)_2C_6H_3](N\text{-}2,6\text{-}C_6H_3\text{-}i\text{-}Pr_2)[OCH_3(CF_3)_2]_2$--.

Signed and Sealed this

Twenty-ninth Day of October 1996

*Attest:*

BRUCE LEHMAN

*Attesting Officer*      *Commissioner of Patents and Trademarks*